United States Patent

Jewell et al.

[11] Patent Number: 5,116,345
[45] Date of Patent: May 26, 1992

[54] STEREOTACTICALLY IMPLANTING AN INTRACRANIAL DEVICE

[75] Inventors: Brian Jewell, Batavia; Hwa-Shain Yeh, Cincinnati, both of Ohio

[73] Assignee: Ohio Medical Instrument Co., Inc., Cincinnati, Ohio

[21] Appl. No.: 619,105

[22] Filed: Nov. 28, 1990

[51] Int. Cl.⁵ .............................. A61B 19/00
[52] U.S. Cl. ................................ 606/130
[58] Field of Search ............. 606/185, 130, 50, 102, 606/172, 79, 80, 87; 128/630, 634, 658, 179, 786

[56] References Cited

U.S. PATENT DOCUMENTS

| | | | |
|---|---|---|---|
| 3,457,922 | 7/1969 | Ray | 606/130 |
| 4,233,979 | 11/1980 | Naser | 606/102 |
| 4,350,159 | 9/1982 | Gouda | 606/130 |
| 4,512,351 | 4/1985 | Pohndorf | 128/786 |
| 4,585,013 | 4/1986 | Harris | 128/786 |
| 4,805,615 | 2/1989 | Carol | 606/130 |
| 4,840,617 | 6/1989 | Osterholm | 604/179 |
| 4,955,891 | 9/1990 | Carol | 606/130 |
| 5,030,223 | 7/1991 | Anderson et al. | 128/630 |

*Primary Examiner*—C. Fred Rosenbaum
*Assistant Examiner*—William Lewis
*Attorney, Agent, or Firm*—Wood, Herron & Evans

[57] ABSTRACT

Apparatus and method for implanting an intracranial device along a predetermined axis into the skull. A support has a bore which is axially alignable on the axis. A drill bit, screwdriver, cannula, and interacranial device are sequentially received in and guided through the bore for drilling an opening in the skull, securing a skull bolt in the opening, inserting a cannula in the opening, and inserting an intracranial device through the cannula in precisely guided movement on the axis. The support and cannula can be removed laterally from the device once in place, to avoid disconnecting an electrical lead to the device.

23 Claims, 3 Drawing Sheets

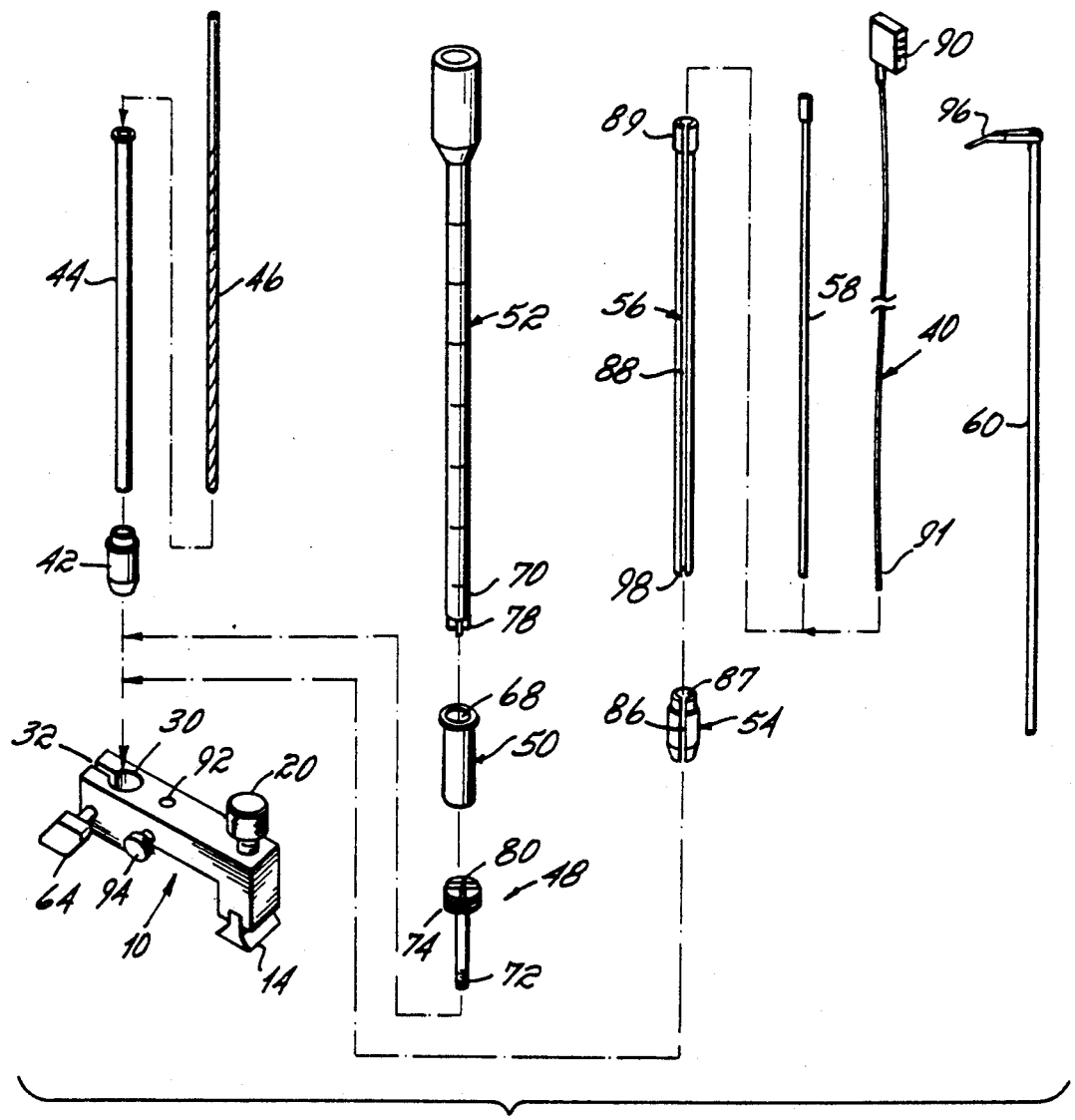
FIG. 2
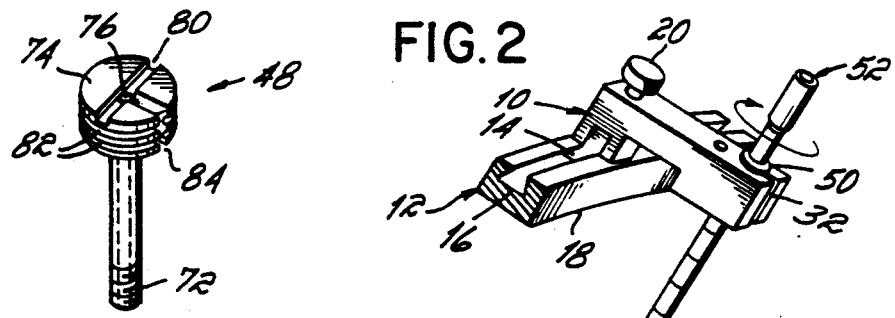
FIG. 2A
FIG. 4
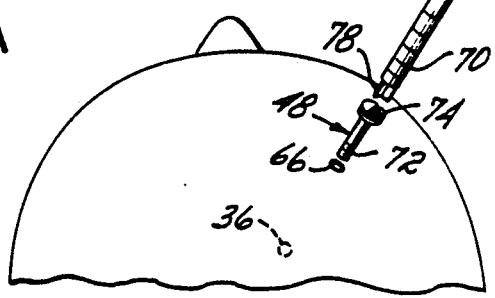

STEREOTACTICALLY IMPLANTING AN INTRACRANIAL DEVICE

FIELD OF THE INVENTION

This invention relates to stereotactically implanting a device such a depth electrode, in the cranium.

BACKGROUND OF THE INVENTION

Stereotactic surgery is the gaining of precise access to a specific point in the body, especially the cranium, of a patient, by reference to an external three dimensional coordinate system. With the development of magnetic resonance imaging ("MRI") and the precise imagining it provides, stereotactic surgery is becoming a diagnostic and therapeutic procedure of choice for many disorders involving the intracranial cavity. By way of illustration, an MRI study can be used to form a three dimensional picture of the brain which defines the positional relationship of neurological structures or which accurately localizes a lesion in the brain. With the aid of stereotactic apparatus the precise position of the lesion or other site within the cranium can be specified with reference to an external reference source that is fixed with respect to the skull. Once the location of the target has been determined with respect to the reference source, inspection and treatment can be carried out more precisely because location of the target within the cranium is accurately specified and precisely accessible.

By way of more specific illustration, Carol U.S. Pat. No. 4,805,615, issued Feb. 21, 1989, discloses a method and apparatus for performing stereotactic surgery, in which there is established a first predetermined geometric relationship between a positioning fixture mounted to the patient's skull, and a scanning table surface upon which the patient is positioned. That geometric relationship is then duplicated in an external or "phantom" fixture. The phantom fixture duplicates the same geometric relationship, but outside the cranium. The phantom fixture includes means for receiving at least a portion of the positioning fixture, and means for establishing a second predetermined geometric relationship between that portion of the positioning fixture and the phantom fixture, so that the second geometrical relationship is identical to the first. The position and slope of the skull at the location where the positioning fixture is attached to it can be duplicated within the phantom fixture. With the target thus pinpointed, it can thereafter be accessed more exactly.

A pending application, Carol Serial No. 111,987, filed Oct. 22, 1987, now U.S. Pat. No. 4,955,891, entitled "Method and Apparatus for Performing Stereotactic Surgery," discloses a related device including an arcuate fixture for use with the phantom fixture of the patent, whereby a medical instrument on the arc fixture can be precisely aligned with the target from a plurality of locations on the skull. The disclosures of the Carol patent and application are incorporated herein by reference.

In various neurosurgical procedures it is desirable to precisely insert or implant a medical instrument or device (referred to as an "intracranial device") at a specified location in the cranium. For example, an electronic device such as a so-called "depth electrode" may be inserted to measure electrical activity at a given point in the brain, or reinserted to the same point at a subsequent time; or a radioactive seed may be implanted at a precise location for treatment of a lesion in the brain.

The stereotactic devices of the Carol patent and application make it possible to establish an imaginary radial axis which extends a predetermined distance directly to the target area in the skull, from an external point. Given such precise location specifying capability, there is also a need for means to insert an intracranial device precisely along a preestablished radial axis from outside the skull, and to implant it at the specified target depth. In cases where the device is removed after treatment, it is desirable to be able later to reinsert the device along the same axis, to the same point. Such insertion involves forming an opening in the cranium; then inserting the device, which may be delicate and/or flexible, to the desired location along a predetermined direction and to a predetermined depth, through the opening. Moreover, it is preferable that any electrical wires connected to the device remain connected throughout the implanting procedure. Thus if a cannula or sleeve is used to guide the insertion of the device, the cannula should be removable from the device without requiring disconnection of any wire to it.

BRIEF DESCRIPTION OF THE INVENTION

This invention provides a method and apparatus whereby an intracranial device can be inserted along a stereotactically defined axis, to a predetermined target area in the intracranial space. The stereotactic apparatus used to define the axis may for example be of the type defined in the Carol patent and/or application, but the invention is not limited to use with that apparatus.

The present apparatus provides means for cutting a cylindrical opening through the skull, along a stereotactically preestablished axis; inserting a cannula (sleeve) through the drilled opening to guide the path of the intracranial device, and removing the cannula without disturbing the device, once implanted, or any electrical connections to it.

More specifically, in preferred form the apparatus of this invention includes a support which is mountable on stereotactic apparatus and having a guide bore in it. The support is aligned by the stereotactic apparatus so that the axis of the bore coincides with a predetermined axis that extends toward a specified situs within the cranium. A drill bit of selected diameter is receivable axially through the bore, drill guide means (preferably in the form of a drill collar or adapter and a drill guide) being used to match the diameter of the drill to the bore. The drill is rotatable and axially translatable through the bore, along the axis. A skull bolt having an axial opening, preferably a Yeh bolt, is aligned and screwed in the drilled skull opening by a driver which is guided and aligned axially through the guide bore A stiff cannula is then inserted through the guide bore and through the axial opening in the bolt, in alignment with the axis, into the patient,s skull. Preferably the cannula is guided by cannula guide means in the form of a cylindrical, split cannula sleeve or holder which fits into the bore. A stylet may be inserted longitudinally through the cannula to stiffen it and to close the axial opening of the cannula during insertion. When the cannula is in place, the stylet is removed and an electrode or other intracranial device is inserted into the brain through the axial opening of the cannula. In the preferred practice of the invention, the cannula is inserted almost to the depth of the target but is stopped just short of it, along the stereotactic axis. The device is pushed a short distance further inwardly from the cannula so that the device passes through virgin tissue to reach the target site. The cannula is then removed, leaving the device in the brain. The cannula is preferably removed from the device by moving the cannula laterally from the device, the cannula having a longitudinal split or slot opening along one side which is wide enough that the device can pass outwardly through it.

DESCRIPTION OF THE DRAWINGS

The invention can best be further described by reference to the following drawings, in which:

FIG. 2 is an exploded diagrammatic view of a preferred form of apparatus in accordance with the invention;

FIG. 2A is an enlarged perspective view of the preferred form of skull bolt used in the invention;

FIG. 3-7 are a series of ciagrammatic perspectives showing the steps of the method of the invention. More specifically, FIG. 3 shows the drilling step;

FIG. 4 shows the insertion of a skull bolt;

FIG. 5 shows insertion of the cannula and stylet into the skull;

FIG. 6 shows the step of implanting an intracranial device; and

FIG. 7 shows the skull with the implanting completed with the leads to the device secured to the skull bolt.

DETAILED DESCRIPTION

Figure 1:
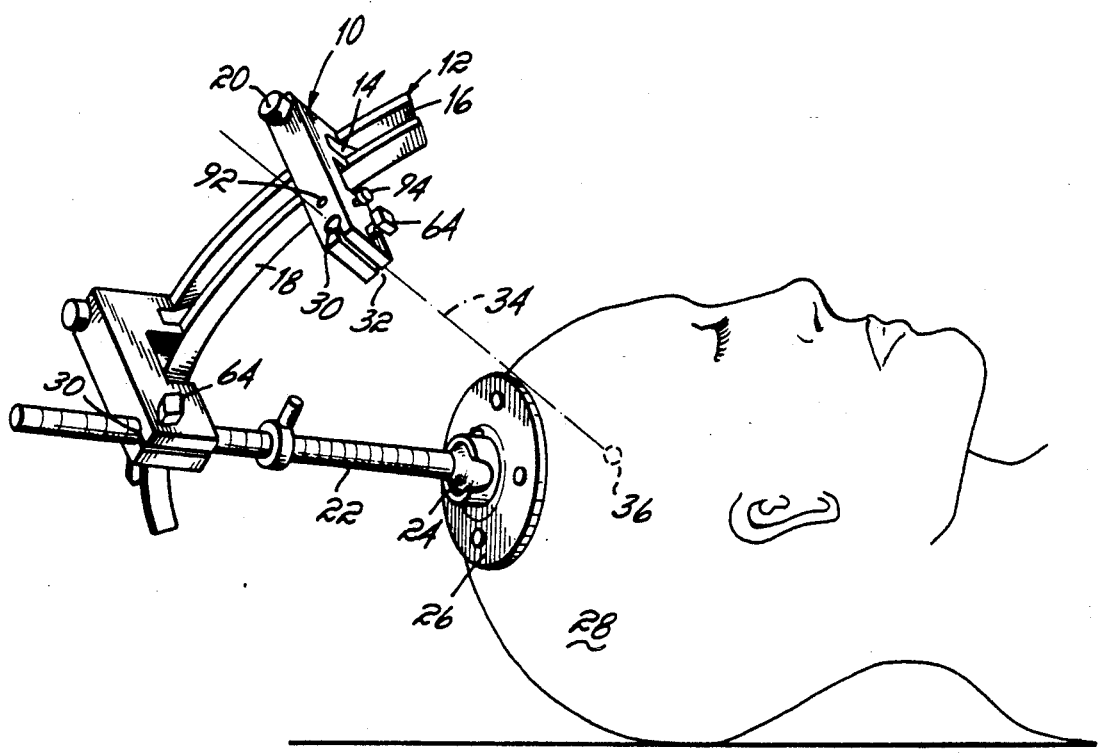
FIG. 1 is a diagrammatic perspective showing a patient having a stereotactic locating fixture secured to the skull, preparatory to insertion of an intracranial device in accordance with the invention.

In the preferred apparatus for practicing the invention, a support or arm 10 is attached to a stereotactic apparatus designated generally by 12. Sterotactic apparatus 12 may, for example be of the type described in Carol patent No. 4,915,891, previously referred to. At an outboard end, support 10 has a cylindrical guide bore 30 through it, with a longitudinal slot 32 extending between bore 30 and the outer end of the support. The support 10 shown for purposes of explanation has a dovetail 14 (Fiq. 2) which can be received in a corresponding dovetail slot 16 in an arc member 18 of stereotactic apparatus 12, and secured in desired position along the arc by a set screw 20. Arc member 18 is supported and fixed on a shaft 22 which has a universal ball joint 24 at its lower end, and is locked in a socket in a skull plate 26. Skull plate 26 is screwed to the skull 28 of a patient, as further described in the Carol application. With arc member 18 so set up, an imaginary line or axis 34 extending through the center of bore 30 will pass through a predetermined target 36 within skull 28. Target 36 may for example be a lesion or tumor.

As best shown in FIG. 2, the preferred apparatus of the invention is a set of tools used with support arm 10 for drilling a skull opening, inserting and securing an intracranial device 40 at target 36 in the skull. The set includes a drill collar 42, drill guide 44, drill bit 46, skull bolt 48, screwdriver sleeve 50, screwdriver 52, cannula holder 54, cannula 56, stylet 58, and clip 60 for supporting device 40.

Figure 3:
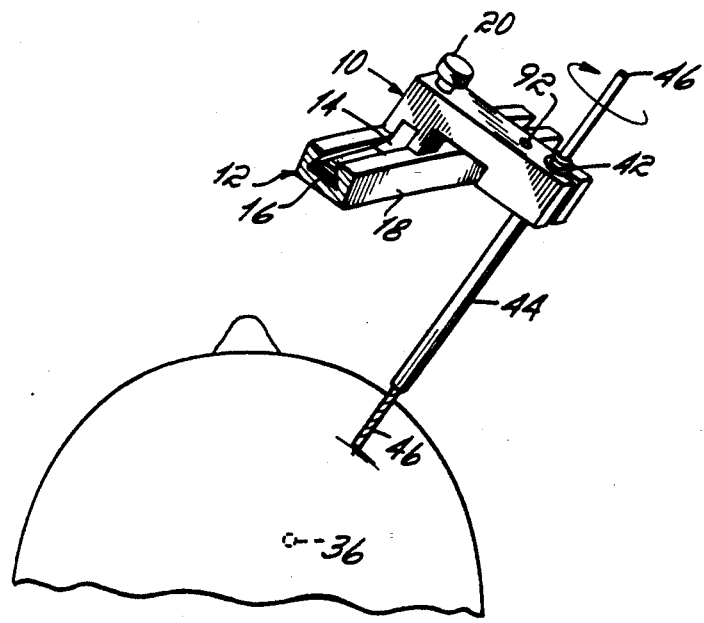
Figure 5:
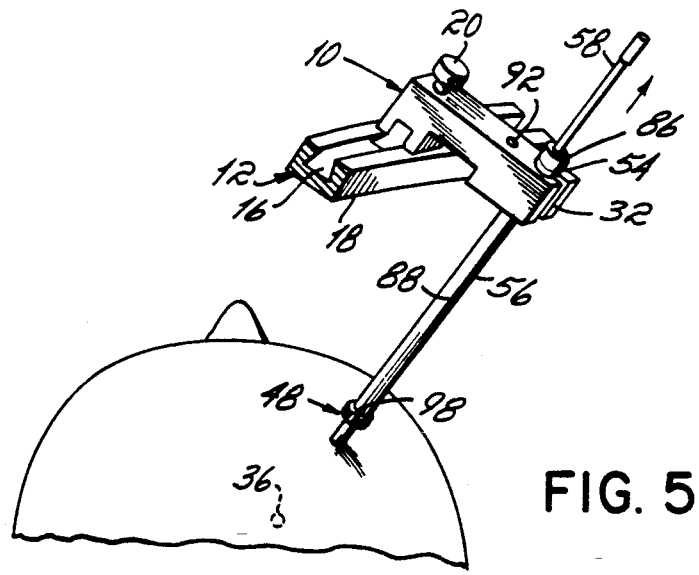

More specifically, the bore 30 is first used to guide and direct drill bit 46 for forming an opening of desired size in the skull, in line with the target (FIG. 3). For that purpose drill collar 42 is inserted to adapt the guide bore to the diameter of the particular bit 46 to be used. Collar 42 has an internal opening which receives an elongated tubular drill guide 44 in which a bit 46 of predetermined size is rotatable and axially movable. With collar 42 inserted in bore 30 and drill guide 44 inserted in the collar, bit 46 can be guided to move along axis 34 toward target 36. Bit 46 may be of a type known per se, for example a conventional 304 stainless steel twist drill. Its diameter of course depends upon the size of opening desired; a 9/64" diameter is often used. When a suitable opening 66 has been bored in the skull, drill bit 46, drill guide 44, and collar 42 are removed from bore 30 and screwdriver sleeve 50 is inserted (FIG. 4). Sleeve 50 has an internal opening 68 sized to receive and guide the shank 70 of screwdriver 52, which is used to thread a skull bolt 48 into the skull.

Bolt 48 has a threaded shank 72, a slotted head 74, and an axial opening 76 (see FIG. 2A). Its shank 72 is threaded externally so as to cut threads in skull opening 66. It is screwed into opening 66 with its axial opening 76 aligned on axis 34, by turning screwdriver 52 while in such alignment. The outside diameter of the screwdriver sleeve 50 interfits in guide bore 30, and screwdriver shank 70 has an outside diameter which is smoothly and rotatably received within the central bore 68 of screwdriver sleeve 50 (FIGS. 2 & 4). Driver 52 has a tip 78 which interfits with a slot 80 in the head 74 of bolt 48 to screw the shank into opening 66. Bolt 48 is preferably a so-called Yeh bolt, known per se, which has several axially spaced grooves 82 around its head 74 and a longitudinal slot 84 which intersects the peripheral grooves 82. The use of these grooves is described hereinafter.

After bolt 48 has been secured in the skull, driver sleeve 50 and driver 52 are removed from the guide bore 30, and cannula holder 54 is inserted. This tubular holder 54 has an outside diameter fitting guide bore 30, an internal opening 87, and is split or slotted longitudinally to provide a sidewise opening 86 for removal of device 40, as will be described. Cannula 56 is a stiff elongated sleeve and has a longitudinal slot 88 which can be aligned with slot 86 of cannula holder 54. Cannula 56 has a stop 89 at its upper end and is preferably graduated with markers along its length to indicate the relative depth of insertion.

Stylet 58 is receivable axially through cannula 56 and is inserted in the cannula before the cannula is inserted through holder 54. Medical device 40, for example a so-called "depth electrode" of type known per se, is a flexible, slender wire having sensors 91 at one end and an electrical connector 90 at the opposite end. The senior end is passed through the axial opening in cannula 56 when stylet has been removed, into the brain.

While dimensions are not critical, the following examples indicate useful relations of diameters (in inches) of the components, in the case of a 9/64" (0.149") drill bit 46.

I.D. guide bore 30—0.502"
O.D. of drill collar 42—4.99
I.D. of opening 62 in drill collar—0.235
O.D. of drill guide 44—0.234
I.D. of drill guide 44—0.149
O.D. of screwdriver sleeve 50—0.500
I.D. of screwdriver sleeve 50—0.377
O.D. of screwdriver shank 70—0.375
O.D. of bolt shank 72—0.160
I.D. of opening 76 in bolt 48—0.084
O.D. of cannula holder 54—0.499
I.D. of cannula holder 54—0.084

O.D. of cannula 56—0.083
I.D. of cannula 56—0.061
width of slot in cannula 56—0.045
O.D. of stylet—0.060
O.D. of device 60—0.059

Figure 6:
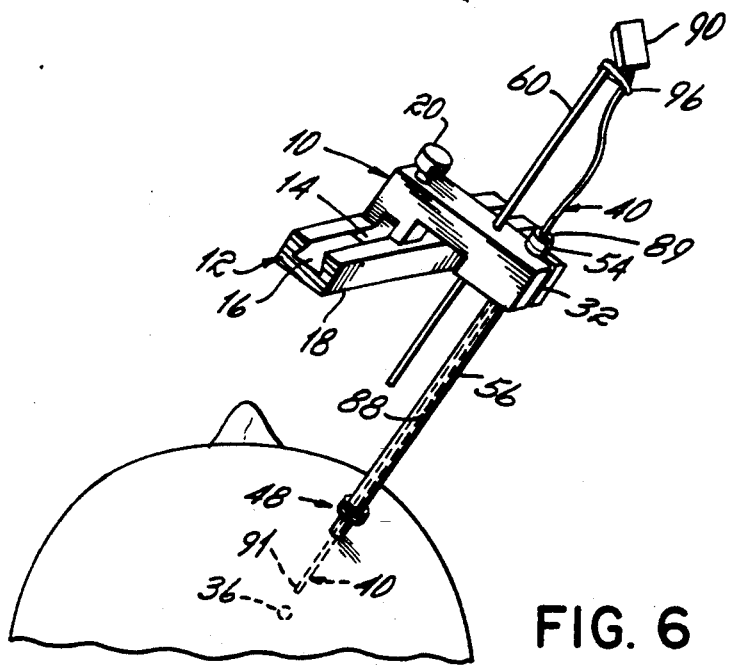

In addition to guide bore 30, support 10 has a secondary aperture 92, provided with a thumb screw 94, which receives a support rod 60 for holding device 40. Rod 60 has a microclip 96 at its upper end and may be inserted in bore 92 to support device 40 (see FIG. 6).

In use of the apparatus, after an opening 66 has been bored in the skull as described above, screwdriver sleeve 50 is inserted in the guide bore 30 and screwdriver shank 70 is inserted through it. A bolt 48 is placed with its threaded shank 72 in alignment between opening 66 and bore 68, below support arm 10, and screwdriver 52 is engaged with bolt slot 80 and turned to thread the bolt into the skull. Driver 52 is then removed from driver sleeve 50 and the sleeve is removed from the support arm. Split cannula holder 54 is next inserted in guide bore 30, and stylet 58 is inserted in cannula 56. The cannula is inserted through the axial opening 87 in split cannula holder 54. Slot 88 in the cannula should be in line with the slot 86 in the cannula holder, and with the slot 32 of support 10.

Figure 7:
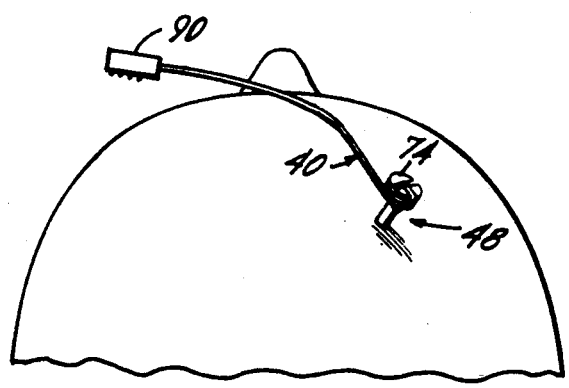

The split cannula and stylet are then pressed into the brain until the tip 98 of the cannula is just a short distance, e.g., two or three millimeters, short of target 36. The stylet is removed from the cannula, and electrode 40 is inserted lengthwise, to target depth, so that the device will pass through virgin tissue to the target. Next, the support 60 for holding device 40 is placed in hole 92, adjusted to desired height, secured with thumb screw 94, and clip 96 is secured onto the wire. The cannula is then slowly retracted from bolt 48. Electrode 40 is clamped with hemostats at the bolt head 74. While holding the support, screw 64 is removed from slot 32, and cannula 56, cannula holder 54 and support arm 32 are removed sidewise from electrode 40 via slots 88, 86, and 32. The wire of device 40 is downturned and wrapped around the grooves 82 and slot 84 in bolt 48, as shown in FIGS. 2A and 7, to secure the device against movement in the skull.

From the foregoing it can be seen that the invention provides a means of accurately making an opening into the skull toward a specified target, fastening a skull bolt in the opening on the predetermined axis, inserting an intracranial device through the bolt to the target, removing the supporting and guiding structure, and securing the leads to the device without disconnecting them during the procedure.

Having described the invention, what is claimed is:

1. Apparatus for stereotactically implanting a flexible intracranial deivce compirsing,
    a support mountable on a stereotactic apparatus, said support having a guide bore alignable on a selected axis toward a target within a patient's skull,
    drill guide menas removably mountable in sid guide bore in alignment with siad axis,
    a drill bit receivable in said drill guide means for rotary and axial movmeent theren, said drill guide means aligning siad bit for drilling a cranial opening along said axis,
    a stiff cannula insertable through siad guide bore and siad cranial opening into the patient's skull, after removal of said bit, and
    a flexibel intracranial device which is insertable longitudinally through said cannula into siad opening,
    said cannula having a longitudinal slot extending from one end to the other thereof, said slot having a width sufficient for lateral removal of siad cannula from siad device.

2. The apaparatus of claim 1 wherein siad cannula is split longitudinally so that siad device is removable laterally from siad cannula.

3. The apparatus of claim 1 further including cannula guide means removably mountable in said guide bore in alignment with said axis for guiding movement of said cannula into said opening.

4. The apparatus of claim 3 wherein said cannula guide means is split longitudinally for lateral removal from said device.

5. The apparatus of claim 1 further including a screwdriver guided by said guide bore and a skull bolt threadable into said opening along said axis by said screwdriver in said guide bore.

6. The apparatus of claim 5 further including a screwdriver guide removably mountable in said guide bore in alignment with said axis,
    said screwdriver having a shank receivable in said screwdriver guide for rotary and axial movement therein.

7. The apparatus of claim 1 further including a skull bolt,
    said cannula being longitudinally slidable through an axial opening in said bolt.

8. The apparatus of claim 7 wherein said skull bolt is a Yeh bolt.

9. The apparatus of claim 1 wherein said drill guide means and cannula have different diameters, and
    said guide bore receives adapters having openings of different diameters for receiving said drill sleeve and cannula.

10. The apparatus of claim 9 wherein said drill guide means includes an elongated sleeve through which said drill can pass, said sleeve being mountable in said guide bore to align said drill on said axis.

11. The apparatus of claim 1 further including a screwdriver sleeve receivable in said guide bore and a screwdriver receivable in said screwdriver sleeve for screwing a skull bolt into said opening, in alignment with said axis.

12. The apparatus of claim 1 further including a stylet axially receivable in said cannula, said stylet being removable for insertion of said device through said cannula.

13. The apparatus of claim 1 where said device is a depth electrode.

14. Apparatus for stereotactically impanting an intracranial device comrsing,
    a support mountable on a stereotactic apparatus, said support having a guide bore alignable on a selected axis toward a target within a patient's skull,
    drill guide menas removably mountable in sid guide bore in alignment with siad axis,
    a drill bit receivable in said drill guide means for rotary and axial movmeent theren, said drill guide means aligning siad bit for drilling a cranial opening along said axis,
    a cannula insertable through siad guide bore and said cranial opening into the patient's skull, after removal of said bit, said annula being split longitudinally so that siad device is removable laterally fro msiad cannula, and
    an intracranial device which is insertble longitudially through siad cannula into siad opening, said guide bore axially receiveing a cannula holder wchich in turn axially receives siad cannula, said cannula holder and guide bore both having longitudinal openings which are alignable with the pslit in said cannula for lateral removal from siad device.

15. Apparatus for stereotactically implanting an intracranial device comprising, a suport mountable on a stereotactic apparatus, said support having a guide bore alignable on a selected axis toward a target within a patient's skull, drill guide means removabley mountable in siad guide bore in alingment with siad axis, a drill bit receivale in siad drill guide means for rotary and axial movement therin, said drill guide means aligning said bit for dirlling a crtanial opening along siad axis, a cannula insertable through said guide bore and said cranial opening into the patient's skull, after removal of siad bit, an intracranial device which is insertable longiudinally through siad cannula into said opening, and a clip for supporting siad device, siad clip carried on a stand which is removably positionable by siad support arm.

16. The apparatus of claim 15 wherein siad clip extends perpendicuarly from siad stand, in line with said guide bore.

17. The method of implanting an intracranial device comprising, positioning a guide externally to the skull so that a bore in said guide is aligned on a predetermined axis through a desired target in the skull, drilling an opening in the skull with a bit passed through and guided by said bore, threading a skull bolt into said opening, said bolt having an axial opening, inserting a cannula into the skull along said axis, said cannula passing through and guided by said bore and said aperture in said bolt, inserting said device into the skull through said cannula and bolt, and removing said cannula from said device and skull.

18. The method of claim 17 wherein said drill is guided by a drill sleeve inserted in said bore.

19. The method of claim 17 wherein said guide is mounted to stereotactic apparatus secured to the skull.

20. The method of claim 17 further wherein said bolt is threaded into said opening by a driver inserted through and guided by said bore.

21. The method of claim 20 wherein said driver is guided by a driver sleeve inserted in said bore.

22. THe method of implanting an intracranial device comprising, positioning a guide externally to the skull so that a bore in siad guide is aligned on a predetermined axis through a desired target in teh skull, drilling an opneing in the skull with a bit passed through and guided by siad bore, threading a skul bolot into said opneing, siad blot having an axial opneing, inserting a cannula into the skull along siad axis, said cannula passing through and guided by said bore and said aperture in siad bolt, inserting siad device into the skull through said cannula and bolt, removing said cannula from said device and skull, and removing electrical leads to said device laterally from siad cannula and siad bore through longitudinal slot openings.

23. The method of implanting an intracranial device comprsing, positioning a guide externally to the skull so that a bore in siad guide is aligned on a predetermined axis through a desired target in teh skull, drilling an opneing in the skull with a bit passed through and guided by siad bore, threading a skul bolot into said opneing, siad blot having an axial opneing, inserting a cannula holder in said bore, inserting a cannula into the skull along siad axis, said cannula passing through and guided by said cannula holder inserted in said bore, and by siad aperture in siad bolt, inserting said device into the skull through said cannula and bolt, and removing said cannula from said device and skull.

* * * * *